US00PP10235P

United States Patent [19]

Adolph

[11] Patent Number: Plant 10,235

[45] Date of Patent: Feb. 10, 1998

[54] PETUNIA PLANT NAMED 'SVEN'

[75] Inventor: Ernest Adolph, Scharrachbergheim, France

[73] Assignee: Plantagen S.A., Scharrachbergheim, France

[21] Appl. No.: 715,639

[22] Filed: Sep. 18, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Assistant Examiner*—Kent L. Bell
*Attorney, Agent, or Firm*—C. A. Whealy

[57] ABSTRACT

A distinct cultivar of Petunia plant named 'Sven', characterized by its white flowers with yellow throat and venation; floriferous with numerous flowers per plant; early flowering; vigorous growth habit and rapid growth rate; spreading plant habit and freely branching; rounded leaf shape; pleasant fragrance; narrow sepals; flowers have good weather resistance; and resistance to phytopathological mildews.

3 Drawing Sheets

The present invention relates to a new and distinct cultivar of Petunia plant, botanically known as *Petunia axillaris*, and hereinafter referred to by the cultivar name 'Sven'.

The new cultivar is a product of a planned breeding program conducted by the inventor in Scharrachbergheim, France. The objective of the breeding program was to create new Petunia cultivars having desirable flower colors, and strong healthy foliage and plants.

The new cultivar originated from a cross made by the inventor of the inventor's proprietary Petunia selection No. 9333, as the male or pollen parent, with the inventor's proprietary Petunia selection No. 9333, as the female or seed parent, in July, 1994.

The cultivar 'Sven' was discovered and selected by the inventor in March, 1995, as a flowering plant within the progeny of the stated cross in a controlled environment in Scharrachbergheim, France. Asexual reproduction of the new cultivar by terminal cuttings taken at Scharrachbergheim, France, has shown that the unique features of this new Petunia are stable and reproduced true to type in successive generations.

The cultivar 'Sven' has not been observed under all possible environmental conditions. The phenotype may vary somewhat with variations in environment such as temperature and light intensity, without, however, any variance in genotype. The following observations, measurements and comparisons describe plants grown in Scharrachbergheim, France, under commercial production conditions.

The following traits have been repeatedly observed and are determined to be the unique characteristics of 'Sven'. These characteristics in combination distinguish 'Sven' as a new and distinct cultivar:

1. White flowers with yellow throat and venation.
2. Floriferous with numerous flowers per plant.
3. Early flowering.
4. Vigorous growth habit and rapid growth rate.
5. Spreading plant habit and freely branching.
6. Rounded leaf shape.
7. Pleasant fragrance.
8. Narrow sepals.
9. Flowers have good weather resistance: tolerant to rain, drought and temperature extremes.
10. Resistant to phytopathological mildews.

The accompanying colored photographs illustrate the overall appearance of the new cultivar, showing the colors as true as it is reasonably possible to obtain in colored reproductions of this type.

The first photograph comprises a top perspective view of a typical hanging basket plant of the cultivar 'Sven'.

The second photograph comprises a close-up view of individual flowers of the cultivar 'Sven'.

The third photograph comprises a close-up view of an individual flower of the cultivar 'Sven'. Flower and foliage colors in the photographs may appear different than the actual colors due to light reflectance.

In the following description, color references are made to The Royal Horticultural Society Colour Chart except where general terms of ordinary dictionary significance are used. Plants used for the description were grown in glass-covered greenhouses during the summer in Scharrachbergheim, France. Measurements are averages or ranges from ten specimens selected at random from five plants.

Botanical classification: *Petunia axillaris* cultivar 'Sven'.

Parentage:

*Male or pollen parent.*—Inventor's *Petunia axillaris* proprietary selection No. 9333.

*Female or seed parent.*—Inventor's *Petunia axillaris* proprietary selection No. 9333.

Propagation:

*Type cutting.*—Terminal vegetative cuttings.

*Time to initiate and develop roots.*—About ten days at 20° C. soil temperature.

*Rooting habit.*—Numerous, fine, fibrous, and well-branched.

Plant description:

*Form.*—Indeterminate, decumbent, diffuse spreading, viscid, glandular pubescent.

*Branching habit.*—Freely branching, usually 6 to 8 branches per stem.

*Plant height (from soil level to top of plant plane).*—7 to 8 cm.

*Spreading area of plant.*—14 to 16 cm.

*Vigor.*—Vigorous, rapid growth rate.

*Crop time.*—10 to 12 weeks from an unrooted cutting to produce a finished and flowering specimen in a 12.5-cm container.

*Foliage description.*—Leaves simple, generally symmetrical and long persisting. Leaves at first whorled, later alternate, somewhat fleshy. Size: Juvenile: Length: 3 to 4 cm. Width: 2 to 3 cm. Mature: Length: 7 to 8 cm. Width: 4 to 5 cm. Shape: Ovate. Apex: Acute. Base: Acute. Margin: Entire. Texture: Smooth. Color: Young foliage upper side: 137C. Young foliage under side: 137D. Mature foliage upper side: 137B. Mature foliage under side: 137D.

*Stem description.*—Diameter: About 2 mm. Internode length: 2 to 4 cm. Color: 137B/137C. Texture: Very pubescent.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall. Flowers self-cleaning.

*Quantity.*—Numerous flowers per plant.

*Flower bud.*—Length: 3.5 to 4.5 cm. Diameter: About 8 mm.

*Corolla.*—Diameter: 5 to 5.5 cm. Height: 5 to 6 cm. Petal quantity: Five, fused. Petal apex: Rounded with sharply acute tip. Margin: Entire, slightly undulate. Texture: Satiny and smooth. Color: Petal color, abaxial surface: 155B. Petal color, adaxial surface: 155B. Petal vein color, abaxial surface: 5A. Petal vein color, adaxial surface: 5A. Throat: 5A.

*Sepals.*—Quantity: Five. Shape: Linear. Apex: Obtuse. Margin: Entire. Aspect: Upright. Color: Adaxial surface: 137C. Abaxial surface: 137D.

*Peduncle.*—Aspect: Erect. Size: Length: 2.5 to 3 cm. Width: About 1 mm. Color: 143D.

*Reproductive organs.*—Stigma above anthers, superior ovary. Stamens: Stamen number: Five. Anther size: About 1 mm. Anther color: 153C. Pollen color: 18C. Pistils: Stigma color: 143C. Style length: About 2 cm.

Disease resistance: Resistant to phytopathological mildews.

Seed Production: Rarely observed.

It is claimed:

1. A new and distinct cultivar of Petunia plant named 'Sven', as illustrated and described.

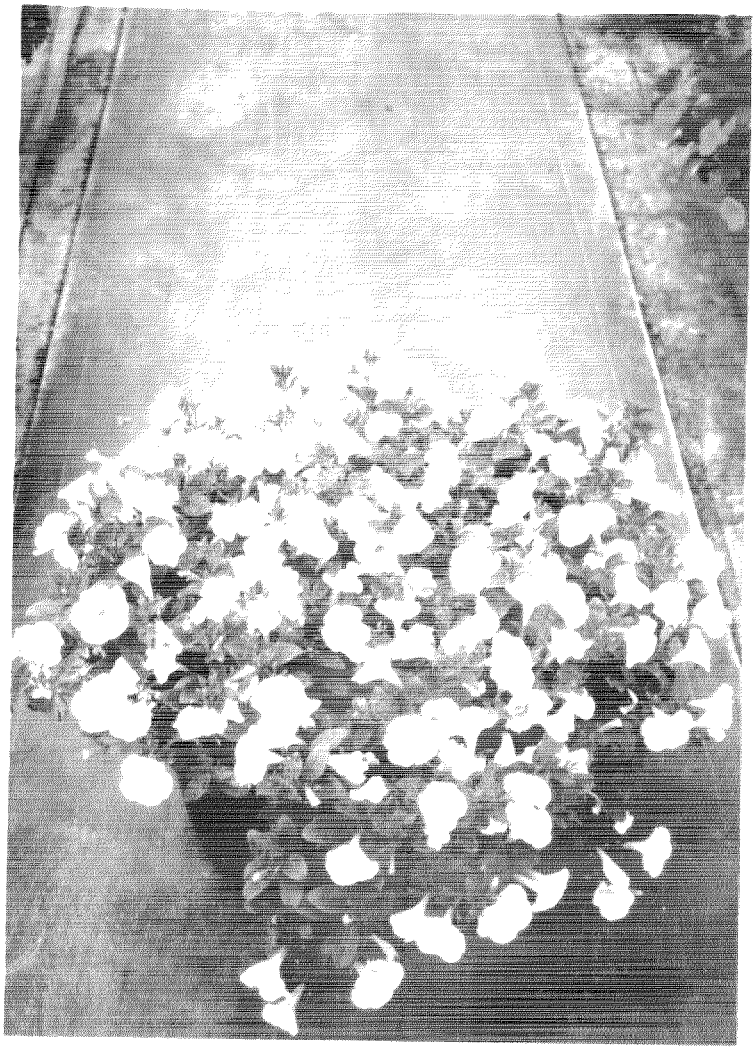

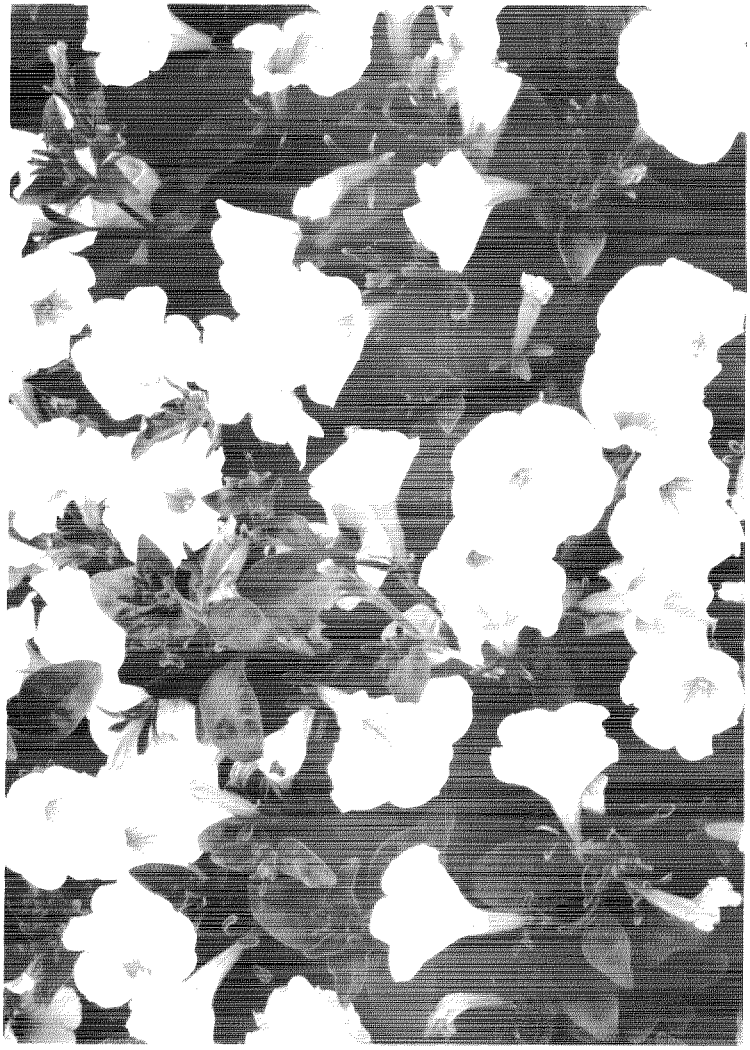

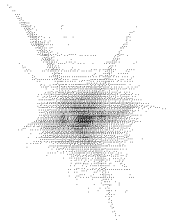

* * * * *